(12) United States Patent
Feferman et al.

(10) Patent No.: US 7,576,045 B2
(45) Date of Patent: Aug. 18, 2009

(54) USE OF VINIC ALCOHOL IN PERSONAL CARE PRODUCTS, COSMETICS AND PERFUMES

(75) Inventors: Israel Henrique S. Feferman, São José Dos Pinhais (BR); Cesar Antônio Veiga, Curitiba (BR)

(73) Assignee: Botica Comercial Farmaceutica Ltda, Sao Jose Dos Pinhais (BR)

( * ) Notice: Subject to any disclaimer, the term of this patent is extended or adjusted under 35 U.S.C. 154(b) by 426 days.

(21) Appl. No.: 11/153,283

(22) Filed: Jun. 15, 2005

(65) Prior Publication Data

US 2005/0276775 A1     Dec. 15, 2005

(30) Foreign Application Priority Data

Jun. 15, 2004   (BR) .................................. 0402260

(51) Int. Cl.
*A61K 8/00*       (2006.01)
*A61K 36/87*      (2006.01)
(52) U.S. Cl. ........................... 510/130; 424/59; 424/65; 424/766; 510/137; 510/158; 510/159; 510/119
(58) Field of Classification Search ................. 510/130; 252/522, 500; 424/59, 65, 766
See application file for complete search history.

(56) References Cited

U.S. PATENT DOCUMENTS

| | | |
|---|---|---|
| 3,852,436 A | 12/1974 | Harich |
| 3,890,212 A | 6/1975 | Harich et al. |
| 4,021,548 A | 5/1977 | Harich et al. |
| 4,021,577 A | 5/1977 | Harich et al. |
| 4,021,578 A | 5/1977 | Harich et al. |
| 4,054,647 A | 10/1977 | Harich et al. |
| 4,064,062 A | 12/1977 | Yurko |
| 4,137,067 A | 1/1979 | Gatzi |
| 4,140,491 A | 2/1979 | Allain et al. |
| 4,178,389 A | 12/1979 | Pilla |
| 4,232,049 A | 11/1980 | Blake |
| 4,244,981 A | 1/1981 | Blake |
| 4,260,527 A | 4/1981 | Trenkle et al. |
| 4,317,410 A | 3/1982 | Prunet |
| 4,339,237 A | 7/1982 | Wang et al. |
| 4,357,360 A | 11/1982 | Light et al. |
| 4,358,462 A | 11/1982 | Takeda |
| 4,368,128 A | 1/1983 | Light et al. |
| 4,371,559 A | 2/1983 | Voisin |
| 4,376,057 A | 3/1983 | Angelo et al. |
| 4,380,552 A | 4/1983 | Gestrelius et al. |
| 4,391,924 A | 7/1983 | Uram, Jr. |
| 4,551,431 A | 11/1985 | Pierce |
| 4,634,588 A * | 1/1987 | Moroe ........................... 424/48 |
| 4,659,697 A | 4/1987 | Tanaka |
| 4,678,603 A * | 7/1987 | Ishii et al. ...................... 512/5 |
| 4,710,468 A | 12/1987 | Sih |
| 4,904,698 A | 2/1990 | Adkins, Jr. et al. |
| 4,909,225 A | 3/1990 | Gonze et al. |
| 4,929,447 A | 5/1990 | Yang |
| 4,945,880 A | 8/1990 | Gonze et al. |
| 4,945,881 A | 8/1990 | Gonze et al. |
| 4,945,882 A | 8/1990 | Brown et al. |
| 4,945,885 A | 8/1990 | Gonze et al. |
| 4,955,345 A | 9/1990 | Brown et al. |
| 4,974,552 A | 12/1990 | Sickafus |
| 5,011,688 A | 4/1991 | Calam et al. |
| 5,034,226 A * | 7/1991 | Beck ........................... 424/401 |
| 5,068,998 A | 12/1991 | Vanysacker |
| 5,104,447 A | 4/1992 | Stewart et al. |
| 5,124,353 A | 6/1992 | Clough et al. |
| 5,132,136 A | 7/1992 | Sato et al. |
| 5,145,595 A | 9/1992 | Morris et al. |
| 5,145,898 A | 9/1992 | Narula et al. |
| 5,198,444 A | 3/1993 | Clough et al. |
| 5,231,358 A | 7/1993 | Kapsokavathis et al. |
| 5,255,661 A | 10/1993 | Nankee, II et al. |
| 5,261,270 A | 11/1993 | Gonze et al. |
| 5,284,597 A | 2/1994 | Rees |
| 5,331,133 A | 7/1994 | Cordier |
| 5,356,641 A | 10/1994 | Bowen et al. |
| 5,362,501 A | 11/1994 | Gopeland et al. |

(Continued)

FOREIGN PATENT DOCUMENTS

| | | |
|---|---|---|
| CN | 1138093 | 12/1996 |
| CN | 1139700 | 1/1997 |
| CN | 1151288 | 6/1997 |
| CN | 1159335 | 9/1997 |
| CN | 1161373 | 10/1997 |
| CN | 1163309 | 10/1997 |
| CN | 1164573 | 11/1997 |
| CN | 1167823 | 12/1997 |
| CN | 1172156 | 2/1998 |
| CN | 1199774 | 11/1998 |

(Continued)

OTHER PUBLICATIONS

Ivsanovic Derwent abstracts, AU 8932774, Nov. 1989.*
Hasegawa et al. JPO abstracts, JP62059206, Mar. 1987.*

*Primary Examiner*—James Seidleck
*Assistant Examiner*—Jane L Stanley
(74) *Attorney, Agent, or Firm*—Buchanan Ingersoll & Rooney PC

(57) ABSTRACT

This invention relates to the use of a vinic alcohol in cosmetic compositions, perfumes and personal care products. The vinic alcohol is characterized as being a product from the grape fermentation followed by purification by distillation, and is used in this invention in total or partial substitution of the conventional ethylic alcohol. The vinic alcohol contains residual substances, which are a characteristic feature of the fermentation of grapes, affording a characteristic odor to the ethanol, contributing to a different olfactory sensorial perception.

22 Claims, No Drawings

U.S. PATENT DOCUMENTS

| | | |
|---|---|---|
| 5,405,606 A | 4/1995 | Campbell et al. |
| 5,534,165 A | 7/1996 | Pilosof et al. |
| 5,578,563 A | 11/1996 | Trinh et al. |
| 5,593,670 A | 1/1997 | Trinh et al. |
| 5,607,668 A | 3/1997 | Campbell et al. |
| 5,607,854 A | 3/1997 | Prahl et al. |
| 5,622,695 A | 4/1997 | Campbell et al. |
| 5,663,134 A | 9/1997 | Trinh et al. |
| 5,698,503 A | 12/1997 | Ward et al. |
| 5,714,137 A | 2/1998 | Trinh et al. |
| 5,783,544 A | 7/1998 | Trinh et al. |
| 5,804,168 A | 9/1998 | Murad |
| 5,804,594 A | 9/1998 | Murad |
| 5,827,511 A | 10/1998 | Campbell et al. |
| 5,891,801 A | 4/1999 | Calam et al. |
| 5,919,991 A | 7/1999 | Subbiah |
| 5,939,060 A | 8/1999 | Trinh et al. |
| 5,972,358 A | 10/1999 | Jampani et al. |
| 5,972,999 A | 10/1999 | Murad |
| 5,976,212 A | 11/1999 | Hartmann |
| 5,997,893 A | 12/1999 | Jampani et al. |
| 6,008,290 A | 12/1999 | Miyoshi et al. |
| 6,022,551 A | 2/2000 | Jampani et al. |
| 6,077,318 A | 6/2000 | Trinh et al. |
| 6,080,416 A | 6/2000 | Jampani et al. |
| 6,124,477 A | 9/2000 | Harris |
| 6,132,788 A | 10/2000 | Zimlich, III |
| 6,146,621 A | 11/2000 | Trinh et al. |
| 6,200,786 B1 | 3/2001 | Huang et al. |
| 6,248,135 B1 | 6/2001 | Trinh et al. |
| 6,248,343 B1 | 6/2001 | Jampani et al. |
| 6,303,678 B1 | 10/2001 | Ziche et al. |
| 6,344,226 B1 | 2/2002 | Zimlich, III |
| 6,358,539 B1 | 3/2002 | Murad |
| 6,358,542 B2 | 3/2002 | Cuomo et al. |
| 6,361,803 B1 | 3/2002 | Cuomo et al. |
| 6,361,815 B1 | 3/2002 | Zheng et al. |
| 6,387,370 B1 | 5/2002 | Yegorova |
| 6,403,086 B1 | 6/2002 | Yegorova |
| 6,410,005 B1 | 6/2002 | Galleguillos et al. |
| 6,440,410 B1 | 8/2002 | Yegorova |
| 6,498,195 B2 | 12/2002 | Rosen et al. |
| 6,506,430 B1 | 1/2003 | Zimlich, III et al. |
| 6,528,053 B1 | 3/2003 | Yegorova |
| 6,565,613 B1 | 5/2003 | Winetzky |
| 6,576,035 B2 | 6/2003 | Hartmann et al. |
| 6,583,152 B2 | 6/2003 | Sosnowski et al. |
| 6,599,554 B1 | 7/2003 | Murakami et al. |
| 6,652,865 B2 | 11/2003 | Benameur et al. |
| 6,676,977 B2 | 1/2004 | Murad |
| 6,690,015 B1 | 2/2004 | Benes et al. |
| 6,713,091 B1 | 3/2004 | Kim |
| 6,713,096 B2 | 3/2004 | Cho |
| 6,750,180 B1 | 6/2004 | Argillier et al. |
| 6,756,013 B1 | 6/2004 | Cornell |
| 6,818,233 B2 | 11/2004 | Perkes |
| 6,833,475 B2 | 12/2004 | Sinha et al. |
| 6,869,623 B2 | 3/2005 | Viamonte, Jr. et al. |
| 6,881,705 B2 | 4/2005 | Garnier et al. |
| 6,890,715 B1 | 5/2005 | Lewis et al. |
| 6,914,175 B2 | 7/2005 | Buchter-Larsen et al. |
| 2002/0102287 A1* | 8/2002 | Shanbrom .......... 424/405 |
| 2003/0108493 A1* | 6/2003 | Henry et al. .......... 424/59 |
| 2003/0161897 A1 | 8/2003 | Shanbrom |
| 2003/0180405 A1* | 9/2003 | Pauly et al. .......... 424/766 |
| 2003/0211788 A1 | 11/2003 | Murakami et al. |
| 2003/0212281 A1 | 11/2003 | Sinha et al. |
| 2004/0265443 A1 | 12/2004 | Beltran et al. |
| 2005/0019430 A1 | 1/2005 | Viamonte, Jr. et al. |
| 2005/0107401 A1 | 5/2005 | Schieweck et al. |
| 2005/0201953 A1 | 9/2005 | Hanada et al. |
| 2005/0208177 A1 | 9/2005 | Tsuruhami et al. |
| 2006/0078568 A1* | 4/2006 | Pauly et al. .......... 424/195.16 |
| 2009/0047372 A1* | 2/2009 | Miller .......... 424/766 |

FOREIGN PATENT DOCUMENTS

| | | |
|---|---|---|
| CN | 1221623 | 7/1999 |
| CN | 1243159 | 2/2000 |
| CN | 1248620 | 3/2000 |
| CN | 1266094 | 9/2000 |
| CN | 1269401 | 10/2000 |
| CN | 1271769 | 11/2000 |
| CN | 1273985 | 11/2000 |
| CN | 1289840 | 4/2001 |
| CN | 1333333 | 1/2002 |
| CN | 1373181 | 10/2002 |
| CN | 1393545 | 1/2003 |
| CN | 1399952 | 3/2003 |
| CN | 1443543 | 9/2003 |
| CN | 1450159 | 10/2003 |
| CN | 1483801 | 3/2004 |
| CN | 1507807 | 6/2004 |
| CN | 1507808 | 6/2004 |
| CN | 1507810 | 6/2004 |
| CN | 1507811 | 6/2004 |
| CN | 1541680 | 11/2004 |
| CN | 1543830 | 11/2004 |
| CN | 1546675 | 11/2004 |
| CN | 1587367 | 3/2005 |
| DE | 10008759 | 11/2001 |
| EP | 0 461 036 B1 | 6/1991 |
| EP | 1 506 717 A1 | 7/2004 |
| FR | 2827297 | 1/2003 |
| GB | 2 337 528 A | 11/1999 |
| GB | 2 359 992 A | 9/2001 |
| JP | 55-111458 | 8/1980 |
| JP | 55-150846 | 11/1980 |
| JP | 56-081377 | 7/1981 |
| JP | 56-106585 | 8/1981 |
| JP | 58-020151 | 2/1983 |
| JP | 58-079913 | 5/1983 |
| JP | 59-213370 | 12/1984 |
| JP | 60-075426 | 4/1985 |
| JP | 60-094903 | 5/1985 |
| JP | 61-172839 | 8/1986 |
| JP | 62-059206 | 3/1987 |
| JP | 62059206 * | 3/1987 |
| JP | 62-267278 | 11/1987 |
| JP | 63-130527 | 6/1988 |
| JP | 63-154607 | 6/1988 |
| JP | 63-258537 | 10/1988 |
| JP | 01-225456 | 9/1989 |
| JP | 01-290621 | 11/1989 |
| JP | 02-048502 | 2/1990 |
| JP | 02-072858 | 3/1990 |
| JP | 02-092266 | 4/1990 |
| JP | 02-221268 | 9/1990 |
| JP | 02-286608 | 11/1990 |
| JP | 02-286609 | 11/1990 |
| JP | 03-067556 | 3/1991 |
| JP | 03-183954 | 8/1991 |
| JP | 03-191800 | 8/1991 |
| JP | 03-232811 | 10/1991 |
| JP | 04-058850 | 2/1992 |
| JP | 04-141080 | 5/1992 |
| JP | 04-308516 | 10/1992 |
| JP | 04-365448 | 12/1992 |
| JP | 05-056773 | 3/1993 |
| JP | 05-084049 | 4/1993 |
| JP | 05-097749 | 4/1993 |
| JP | 05-097755 | 4/1993 |
| JP | 05-186450 | 7/1993 |
| JP | 06-046794 | 2/1994 |

| | | | | | | |
|---|---|---|---|---|---|---|
| JP | 07-046966 | 2/1995 | | MD | 2408 F | 3/2004 |
| JP | 07-109230 | 4/1995 | | NZ | 524814 | 8/2004 |
| JP | 08-023954 | 1/1996 | | RU | 109046 | 4/1998 |
| JP | 08-038152 | 2/1996 | | RU | 2109044 | 4/1998 |
| JP | 8038152 | 2/1996 | | RU | 2110566 | 5/1998 |
| JP | 08-168378 | 7/1996 | | RU | 2110567 | 5/1998 |
| JP | 08-256693 | 10/1996 | | RU | 2112027 | 5/1998 |
| JP | 09-040547 | 2/1997 | | RU | 2115707 | 7/1998 |
| JP | 10-028550 | 2/1998 | | RU | 2119947 | 10/1998 |
| JP | 10-036276 | 2/1998 | | RU | 2123518 | 12/1998 |
| JP | 10-120520 | 5/1998 | | RU | 2129151 | 4/1999 |
| JP | 10-120545 | 5/1998 | | RU | 2129154 | 4/1999 |
| JP | 10-158145 | 6/1998 | | RU | 2129155 | 4/1999 |
| JP | 10-158690 | 6/1998 | | RU | 2130059 | 5/1999 |
| JP | 10-182475 | 7/1998 | | RU | 2131916 | 6/1999 |
| JP | 11-075717 | 3/1999 | | RU | 2131917 | 6/1999 |
| JP | 11-221022 | 8/1999 | | RU | 2134293 | 8/1999 |
| JP | 11-228428 | 8/1999 | | RU | 2134294 | 8/1999 |
| JP | 11-276150 | 12/1999 | | RU | 2145632 | 2/2000 |
| JP | 2000-026306 | 1/2000 | | RU | 2148985 | 5/2000 |
| JP | 2000-034243 | 2/2000 | | RU | 2155216 | 8/2000 |
| JP | 2000-041639 | 2/2000 | | RU | 2160775 | 12/2000 |
| JP | 2000-080025 | 3/2000 | | RU | 2163926 | 3/2001 |
| JP | 2000-125823 | 5/2000 | | RU | 2170251 | 7/2001 |
| JP | 2000-159681 | 6/2000 | | RU | 2178438 | 1/2002 |
| JP | 2000-344655 | 12/2000 | | RU | 2186099 | 7/2002 |
| JP | 2004-018470 | 1/2004 | | RU | 2188861 | 9/2002 |
| JP | 2004-113125 | 4/2004 | | RU | 2188862 | 9/2002 |
| JP | 2004-147612 | 5/2004 | | RU | 2198208 | 2/2003 |
| JP | 2004-315462 | 11/2004 | | RU | 2198917 | 2/2003 |
| MD | 1877 F | 3/2002 | | RU | 2219229 | 12/2003 |
| MD | 1927 F | 5/2002 | | RU | 2221035 | 1/2004 |
| MD | 1945 F | 6/2002 | | RU | 2233168 | 7/2004 |
| MD | 1970 F | 7/2002 | | RU | 2233873 | 8/2004 |
| MD | 2039 F | 11/2002 | | WO | WO 00/40628 | 7/2000 |
| MD | 2077 F | 1/2003 | | WO | WO 00/51445 A3 | 9/2000 |
| MD | 2084 | 1/2003 | | WO | WO 01/11988 A3 | 2/2001 |
| MD | 2103 F | 2/2003 | | WO | WO 01/26669 A1 | 4/2001 |
| MD | 20010177 | 3/2003 | | WO | WO 03/078562 A1 | 9/2003 |
| MD | 2337 | 12/2003 | | WO | WO 2004/050819 A1 | 6/2004 |
| MD | 2338 F | 12/2003 | | WO | WO 2004/108150 | 12/2004 |
| MD | 2339 F | 12/2003 | | WO | WO 2005/016363 A1 | 2/2005 |
| MD | 2383 F | 2/2004 | | WO | WO 2005/044025 A1 | 5/2005 |
| MD | 2384 F | 2/2004 | | | | |

* cited by examiner

USE OF VINIC ALCOHOL IN PERSONAL CARE PRODUCTS, COSMETICS AND PERFUMES

This application claims priority to the parent Brazilian application PI 0402260, entitled "Use of Vinic Alcohol in Personal Care Products, Cosmetics and Perfumes," filed on Jun. 15, 2004.

FIELD OF THE INVENTION

This invention deals with the use of a specific type of ethyl alcohol, the vinic alcohol, in personal care products, cosmetics and perfumes, with a view to affording drying properties, volatility, astringency, cleaning, solubility of other ingredients, antimicrobial action, etc. The use of this invention results in a different product, owing to the characteristic odor of the vinic alcohol and to its contribution to the final olfactory sensorial perception.

BACKGROUND OF THE INVENTION

The cosmetic preparations, the personal care products and the perfumes represent a class of products for affording cleaning protection, treatment, coloring, fragrance, deodorization, among other benefits of the skin, mucous membranes and hair.

Cosmetics are products for an external use, intended for protecting or embellishing the different parts of the body, such as creams and beauty lotions, hand creams and alike, facial masks, milky or creamy solutions, astringents, hand lotions, makeup, cosmetic oils, sunscreen preparations, suntanning preparations and the like, capillary dyes, hair coloring agents, preparations for waving and fixing hair, hair sprays, brilliantine and the like, capillary lotions, depilatories, nail preparations and the like.

Personal care products are understood to be products for external use, antiseptic or not, intended for body cleaning or disinfection, comprising soaps, shampoos, hair conditioning preparations, dentifrice, mouth rinsers, antiperspirants, deodorants, shaving and aftershaving products, etc.

As perfumes, they are understood to be products of an aromatic composition, obtained from natural or synthetic substances, which, in concentrations and appropriate vehicles, have the final purpose of affording fragrance to people, objects or environment, including the extracts, toilet water, the creamy perfumes, the bath preparations and environmental fragrances, manufactured in liquid, gelled, viscous or solid form.

These kinds of compositions usually use the ethylic alcohol in view of its refreshing benefits, drying time, volatilization, preservation, solubility, etc.

However, the commonly used ethyl alcohol, in spite of its beneficial features for this sort of formulation, shows a characteristic and pronounced odor, and may affect the olfactory perception of the products, and, for several times, releasing an odor characterized as piquant or pungent. As far as the perfumes, deodorants, after-shaving lotions and other sorts of formulation are concerned, where the concentration of ethanol is considerable, possibly reaching up to 90%, the ethanol conventionally used may interfere with the performance of the fragrances. This may imply an olfactory perception less pleasant than the odor shown by the fragrance in its pure state, owing to the perception together with the piquant or pungent odor of the ethanol.

As the ethanol is an ingredient not easily replaceable by other solvents in its applications, it is highly used, in spite of its olfactory inconveniences.

In this area, there is the particular interest in using a type of alternative ethanol, enabling the development of formulations presenting the drying benefit of the volatility and suitable refreshment, without showing the inconvenient pungent odor, which is a feature of the conventional ethanol and, further, where the ethanol may contribute to making the olfactory perception more pleasant, through perfectly combining the fragrance and other base components, composing a different product. Additionally, this alternative ethanol, when used in personal care products, cosmetics or perfumes, should not cause allergic reactions or irritations on the skin and mucous membranes, which would make unfeasible its use. The combination of these features represents the built-in art in the development of this sort of application.

Document EP0196340B1 protects a cosmetic composition containing conventional ethanol modified through the contact with a solid residue of alcoholic fermentation of grapes, obtained from the producing process of wine. It discloses, as a major object, the removal of the pungent odor present in ethanol, and may, for this purpose, use the ethylic alcohol derived from the chemical synthesis or fermentation of several substrates. Differently from this invention, it does not make use of the vinic alcohol obtained from the fermentation of grapes, which contributes with a specific odor for the olfactory perception of the compositions.

Patent JP61204116A2 protects the application of wines treated with calcium salts in deo-colognes and perfumes, with a view to masking the irritating odor of ethanol and, further, contributing to the moisturization of the skin, owing to the presence of saccharides, amino acids and peptides. Differently from this invention, it does not use the vinic alcohol obtained from the grape fermentation, rather the wine in its full state, bringing along other molecules, which might injure the color and cleanliness of the final composition.

BRIEF DESCRIPTION OF THE INVENTION

This invention discloses the application of a specific variation of ethanol (ethyl alcohol) in personal care products, perfumes and cosmetics. The compositions derived from this invention contain, combined with this specific ethanol, conventionally used ingredients for the formulation of products having distinct purposes. The ethanol may be used for the purpose of promoting the volatility of the fragrance for making feasible the olfactory perception, or, then, performing the functions of promoting the sensation of refreshment, astringency, cleanliness or acting on the preservation of the formulation, or as a solubilizer.

The ethanol conventionally used in the cosmetic industry for personal care products and perfumes, derives mainly from the fermentation of vegetables rich in sugars and amides, mainly sugar cane, beet, corn, rice, among other cereals. Over the time of fermentation, there may occur the formation of byproducts, such as glycerin and the organic acids. In the personal care products, cosmetics and perfumes industries, the alcohol is normally purified in order to prevent influence from these byproducts in the final product.

Another way of the conventional production of ethanol is the synthetic one, from acetylene or ethylene derived from petroleum by a gaseous synthesis (CO+0), among other mechanisms of synthesis.

DETAILED DESCRIPTION OF THE INVENTION

This invention mainly features the innovating application of the vinic alcohol, partially or totally replacing the conventional ethyl alcohol in personal care products, cosmetics or perfumes. The application of the vinic alcohol is known and commonly used in the alcoholic beverage industry; one of the main applications is that of adjusting the alcoholic degree of the beverages. The vinic alcohol is the ethylic alcohol resulting from the fermentation of only grapes (*Vitis vinifera* sp), wherein there occurs the transformation of the sugars by microorganisms, resulting in a must which is later submitted to distillation. At this stage, in view of the fact of the must components present different boiling points, the first steams are always produced by more volatile elements, released from the original liquid mass. This is the case of the ethyl alcohol, which carries along characteristic molecules from the material used as a fermentation source or from the byproducts. This feature makes the vinic alcohol an interesting product from the olfactory point of view, making it different from the alcohol derived from other biological or synthetic sources, resulting in a pleasant olfactory combination, when harmonizing with the fragrances and other raw materials of the product base.

The vinic alcohol, by way of example, was applied to a cologne deodorant in comparison with the conventional ethyl alcohol, within the following base formulation:

| Ingredients | Conventional Formulation A (% m/m) | Formulation B Object of this Invention (% m/m) |
|---|---|---|
| Fragrance | 10.00 | 10.00 |
| Water | 10.00 | 10.00 |
| Triclosan | 0.05 | 0.05 |
| BHT | 0.05 | 0.05 |
| Benzophenone-2 | 0.10 | 0.10 |
| Sugar cane ethylic alcohol | Qsp 100 | — |
| Vinic alcohol | — | Qsp 100 |

These prototypes have been submitted to a triangular evaluation, performed by a panel of technicians specialized in olfactory evaluations. The statistic analysis of the results was carried out on the basis of the binomial distribution and the results are depicted in the table below:

| Perception of the difference by the technicians | Frequency (total of 23 technicians) | % |
|---|---|---|
| Yes | 21 | 91 |
| No | 2 | 9 |

After evaluating the results of this panel, it was concluded that the combination of vinic alcohol with the fragrance showed an easy perceptible difference in relation to the use of the sugar cane ethylic alcohol. Further, the pungent odor of the ethanol was less noticed in the vinic alcohol-containing formulation.

Ipso facto, the present invention does not offer only an application of ethyl alcohol with a view to improving volatilization of the fragrance, affording refreshment, preservation, solubilization of ingredients, cleanliness, astringency, etc. The invention also discloses the innovative application of a specific ethylic alcohol, the vinic alcohol, having differentiated olfactory features, in combination with the olfactory features in the fragrance and other base raw materials, in the formulation of personal care products, perfumes and cosmetics. It further shows an important conceptual contribution for the development and disclosure of products, as it acts as a link between the actual technical benefits and the pleasant aspect of the art of production of wines, exploited and directed to the consumers of personal care products, cosmetics and perfumes.

The compositions disclosed in this invention are obtained from the incorporation of vinic alcohol in concentrations from 0.1% to 99% in bases of personal care products, cosmetics or perfumes. Its use may be further combined with the ethyl alcohol resulting from other sources, such as fermentation of other substrates or chemical synthesis.

A fragrance, aromatic composition of natural and/or synthetic ingredients or essential oils from plants, may be incorporated in concentrations from 0.01% to 30% by weight relating to the total weight of the composition.

Preserving substances may be included, according to this invention.

Vitamins, such as tocopherol or tocopherol acetate, retinol palmitate or other active ingredients, such as antioxidant agents, antiinflammatory and vegetable extracts may further be included with a view to promoting the skin treatment.

For protecting the compositions from oxidation, antioxidant agents may be added. As examples, we may cite butylated hydroxytoluene (BHT), butylated hydroxyanisol (BHA), vegetable antioxidants or others, or the blending of the same.

The obtainment of the additional property of sun protection of the formulation of the invention is managed through the presence of inorganic pigments or the inclusion of a set of organic sunscreens, such as 2-ethylhexyl p-methoxycinnamate, butyl methoxydibenzoylmethane or others and blends of the same, properly solubilized in their suitable solvents.

The use of conventional ethanol may be performed, provided that partially combined with the vinic alcohol.

Components of an oily nature, such as mineral oils, their fractions and byproducts, hydrocarbons, glycerides, esters and cosmetic ethers, silicones, elastomers, Guebert alcohols, vegetable oils, acids and fatty alcohols, among others, and mixtures of the same, may also be used, as well as surfactants, such as emulsifiers or solubilizers.

Thickening agents, such as gums from vegetable or biotechnological origins, acrylates, styrene polymers, celluloses and mixtures of the same, among others, may be used.

Moistening ingredients and humidifiers, such as 10 glycols, polysaccharides, proteins or fractions of the same, among others, may be used.

Coloring substances may be added for modifying the aspect of the product.

This invention may further contain suspended particles, such as iron oxide, mica, polyethylene terephthalate (glitters), silica derivatives, titanium dioxide, zinc oxide, among others, as well as the respective mixtures, with a view to protecting the skin or mucous membranes and further as for ornaments.

The following examples illustrate the invention. The materials are combined and the amounts are represented in percentage by weight, on the basis of the total weight of the composition.

EXAMPLE I

| Cologne Deodorant | Concentration |
|---|---|
| Fragrance or essential oils | 2.0%-18.0% |

EXAMPLE I-continued

| Cologne Deodorant | Concentration |
|---|---|
| Sunscreen Agent | 0.01%-1.0% |
| Antioxidant | 0.01%-0.5% |
| Preservative (triclosan or others) | 0.05%-0.3% |
| Water | 8.0%-20% |
| Vinic alcohol | 40%-90% |

EXAMPLE II

| Sunscreen Gel | Concentration |
|---|---|
| Fragrance or essential oils | 0.01%-30% |
| Antioxidant | 0.01%-1% |
| Sunscreen agent | 0.01%-25% |
| Vitamins, vegetable extracts or other active ingredients | 0.01%-3% |
| Humectant | 0.01%-10% |
| Water | 0.1%-20% |
| Vinic Alcohol | 1%-90% |
| Ethyl alcohol from sugar cane | 1%-90% |

This invention is not limited to the representation herein commented on or illustrated, and must be understood in its broad scope. Many modifications and other embodiments of the invention will come to the mind of those skilled in the art, to which this invention belongs, having the benefit of the teaching submitted in the previous descriptions. Moreover, it is to be understood that the invention is not restricted to the specific form exhibited and that modifications and other forms are understood as incorporated into the scope of the claims attached. Even though specific terms are used herein, we have done so in a generic and descriptive manner and not for a purpose of restriction.

The invention claimed is:

1. A composition comprising a vinic alcohol distillate and at least one material selected from the group consisting of a fragrant aromatic composition, an essential plant oil, a vitamin, an antioxidant agent, an anti-inflammatory agent, a vegetable extract, an inorganic photoprotector, an organic photoprotector, a component having an oily nature, a surfactant, a thickening agent, a moisturizer, a humectant, a coloring agent, suspended particles, and an alcohol from a source other than grapes, wherein the vinic alcohol distillate is a distillate of grape must comprising ethyl alcohol and volatile byproducts of the must and the composition is formulated as a personal care product, a cosmetic or a perfume.

2. The composition of claim 1, wherein said composition comprises from 0.1% to 99% of said vinic alcohol distillate.

3. The composition of claim 1, wherein said composition comprises from 1% to 90% of said vinic alcohol distillate.

4. The composition of claim 1, wherein said composition comprises from 40% to 90% of said vinic alcohol distillate.

5. The composition of claim 1, wherein said composition comprises from 0.01% to 30% of said fragrant aromatic composition and/or said essential plant oil.

6. The composition of claim 1, wherein said fragrant aromatic composition is natural.

7. The composition of claim 1, wherein said vitamin is tocopherol, tocopherol acetate or retinol palmitate.

8. The composition of claim 1, wherein said an antioxidant agent is butylated hydroxytoluene, butylated hydroxyanisol or a vegetable antioxidant.

9. The composition of claim 1, wherein said organic photoprotector is 2-ethylhexyl p-methoxycinnamate or butyl methoxydibenzoylmethane.

10. The composition of claim 1, wherein said component having an oily nature is selected from the group consisting of mineral oils, mineral oil fractions, hydrocarbons, glycerides, esters and cosmetic ethers, silicones, elastomers, Guebert alcohols, vegetable oils, acids, fatty alcohols, and mixtures thereof.

11. The composition of claim 1, wherein said a surfactant is an emulsifier.

12. The composition of claim 1, wherein said a thickening agent is a gum from vegetable or biological origin, an acrylate, a styrene polymer, a cellulose or mixtures thereof.

13. The composition of claim 1, wherein said moisturizer or humectant is a glycol, a polysaccharide, a protein or mixtures thereof.

14. The composition of claim 1, wherein said suspended particles are iron oxide, mica, polyethylene terephthalate, silica derivatives, titanium dioxide, zinc oxide, or mixtures thereof.

15. The composition of claim 1, wherein said alcohol from a source other than grapes is obtained from biological sources.

16. The composition of claim 1, wherein said alcohol from a source other than grapes is obtained from vegetables, sugar cane, beets, corn, rice and other cereals.

17. The composition of claim 1, wherein said composition is formulated as a cosmetic in a form selected from the group consisting of creams, beauty lotions, hand creams, facial masks, milky or creamy solutions, astringents, hand lotions, makeup, cosmetic oil, sunscreen preparations, suntanning preparations, hair dyes, hair coloring agents, preparations for waving and fixing hair, hair sprays, brilliantine, hair lotions, depilatories and nail preparations.

18. The composition of claim 1, wherein said composition is formulated as a personal care product in a form selected from the group consisting of soaps, shampoos, hair fixatives, dentifrice, mouth rinses, antiperspirants, deodorants, shaving products and after-shaving products.

19. The composition of claim 1, wherein said composition is formulated as a perfume in a form selected from the group consisting of an extract, toilet water, a creamy perfume, a bath preparation and environmental fragrances; wherein the perfume is in a liquid, gelled, viscous or solid form.

20. The composition of claim 1, wherein said fragrant aromatic composition is synthetic.

21. The composition of claim 1, wherein said a surfactant is a solubilizer.

22. The composition of claim 1, wherein said alcohol from a source other than grapes is obtained from synthetic sources.

* * * * *

UNITED STATES PATENT AND TRADEMARK OFFICE
CERTIFICATE OF CORRECTION

| | |
|---|---|
| PATENT NO. | : 7,576,045 B2 |
| APPLICATION NO. | : 11/153283 |
| DATED | : August 18, 2009 |
| INVENTOR(S) | : Feferman et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 699 days.

Signed and Sealed this

Seventh Day of September, 2010

David J. Kappos
*Director of the United States Patent and Trademark Office*